US009314010B2

(12) United States Patent
Moreto et al.

(10) Patent No.: US 9,314,010 B2
(45) Date of Patent: Apr. 19, 2016

(54) ENCLOSURES AND METHODS FOR THE MASS DELIVERY OF LIVING BIOLOGICAL PEST CONTROL AGENTS AND METHOD OF MAKING THE SAME

(71) Applicant: EMBRAER S.A., São José dos Campos/SP (BR)

(72) Inventors: José Roberto Moreto, Botucatu (BR); Gabriel Barroso De Araujo, Botucatu (BR); Caio Borges Arias, Botucatu (BR)

(73) Assignee: EMBRAER S.A., São José dos Campos—SP (BR)

(*) Notice: Subject to any disclaimer, the term of this patent is extended or adjusted under 35 U.S.C. 154(b) by 73 days.

(21) Appl. No.: 14/077,431

(22) Filed: Nov. 12, 2013

(65) Prior Publication Data

US 2015/0128482 A1 May 14, 2015

(51) Int. Cl.

| | |
|---|---|
| ***A01M 1/20*** | (2006.01) |
| ***A01M 17/00*** | (2006.01) |
| ***A01M 99/00*** | (2006.01) |
| ***B29C 65/00*** | (2006.01) |
| ***B29D 23/00*** | (2006.01) |
| ***A01K 67/033*** | (2006.01) |
| *B29L 23/00* | (2006.01) |
| *B29K 101/00* | (2006.01) |

(52) U.S. Cl.
CPC .............. *A01M 17/00* (2013.01); *A01K 67/033* (2013.01); *A01M 99/00* (2013.01); *B29C 66/00* (2013.01); *B29D 23/00* (2013.01); *B29K 2101/00* (2013.01); *B29L 2023/00* (2013.01)

(58) Field of Classification Search
CPC ...... A01M 17/00; A01M 99/00; B29C 66/00; B29D 23/00; B29L 2023/00
USPC ........................................................ 43/132.1
See application file for complete search history.

(56) References Cited

U.S. PATENT DOCUMENTS

| | | | | |
|---|---|---|---|---|
| 1,965,953 | A * | 7/1934 | Curtis | 264/130 |
| 3,209,983 | A * | 10/1965 | Bellezanne | 383/113 |
| 3,442,845 | A | 5/1969 | Spiros et al. | |
| 3,921,333 | A | 11/1975 | Clendinning et al. | |
| 4,260,108 | A | 4/1981 | Maedgen, Jr. | |
| 4,418,647 | A * | 12/1983 | Hoffman | 119/6.6 |
| 4,478,661 | A * | 10/1984 | Lewis | 156/92 |
| 4,646,683 | A * | 3/1987 | Maedgen, Jr. | 119/6.5 |
| 5,015,475 | A * | 5/1991 | Kapp et al. | 424/405 |
| 5,794,847 | A * | 8/1998 | Stocker | 239/8 |
| 6,626,313 | B2 | 9/2003 | Herbstreit et al. | |
| 2006/0016905 | A1 * | 1/2006 | Roreger et al. | 239/34 |
| 2009/0152295 | A1 * | 6/2009 | May et al. | 222/129 |
| 2012/0054974 | A1 * | 3/2012 | Hurwitz | 15/167.1 |

FOREIGN PATENT DOCUMENTS

MU MU8701832-2 4/2009

* cited by examiner

*Primary Examiner* — Christopher P Ellis
*Assistant Examiner* — Jessica Wong
(74) *Attorney, Agent, or Firm* — Nixon & Vanderhye P.C.

(57) ABSTRACT

Enclosures for mass delivery of a living biological pest control agent according to the embodiments disclosed herein include a body section having a generally cylindrical wall with opposed ends defining an interior surface, parasitized eggs of a living biological pest control agent (e.g., an endoparasitic insect) adhered to the interior surface of the wall, and at least one egress opening to allow the pest control agent to exit the body section to an exterior environment.

3 Claims, 4 Drawing Sheets

Figure 1:
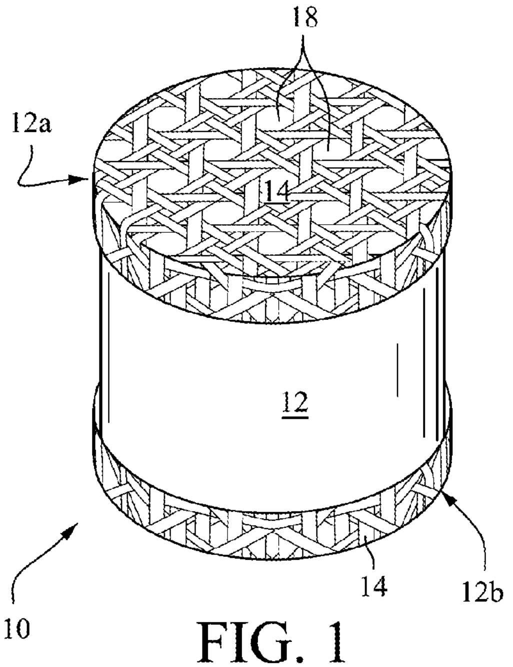

ENCLOSURES AND METHODS FOR THE MASS DELIVERY OF LIVING BIOLOGICAL PEST CONTROL AGENTS AND METHOD OF MAKING THE SAME

FIELD

The embodiments disclosed herein relate generally to enclosures and methods which permit living biological pest control agents (e.g., endoparasitic insect eggs) to be mass delivered to geographical areas in need of pest control (e.g., by conventional air drop techniques) and to the methods whereby such enclosure are made.

BACKGROUND AND SUMMARY

The use of endoparasitic insect eggs, specifically parasitized *Trichogramma* eggs, as a means to control pests in agricultural areas is well known. For example, it has been previously proposed by U.S. Pat. No. 4,260,108 (the entire content of which is incorporated hereinto by reference) that masses of *Trichogramma* eggs can be air-dropped over areas in need of insect pest control. U.S. Pat. No. 6,626,313 and BR MU8701832-2 (the entire contents of each being expressly incorporated hereinto by reference) each disclose enclosures of relatively complex construction that may be employed as a means to protect the parasitized eggs to allow for air-drop delivery and incubation of the eggs such that adult endoparasitoids may emerge and continue the parasitic egg-laying cycle (thereby assisting in control of insect pests in the treated area).

What has been needed, however, are improved enclosures that could readily be fabricated at reasonably low costs. It is toward providing such enclosures that the embodiments disclosed herein are directed.

In general, enclosures for mass delivery of a living biological pest control agent according to the embodiments disclosed herein include a body section having a generally cylindrical wall with opposed ends defining an interior surface, parasitized eggs of a living biological pest control agent (e.g., an endoparasitic insect such as *Trichogramma*) adhered to the interior surface of the wall, and at least one egress opening to allow the post-hatched living pest control agent to exit the body section to an exterior environment following.

According to one embodiment, at least one or both of the opposed closed ends may be covered by a woven fabric material such that the fabric material defines a plurality of egress openings.

Another embodiment will include at least one or both of the ends having a generally conical neck region which defines the egress opening.

According to other embodiments, opposed crimped regions are provided which close each of the opposed ends of the cylindrical body section. At least one egress opening may thus be formed through the cylindrical body section or may be formed through at least one of the crimped ends.

The enclosures of the embodiments disclosed herein are most preferably formed of a biodegradable polymer (e.g., a cellulosics polymeric material, such as cotton-based or wood pulp-based polymeris or starch-based polymeric material). The parasitized eggs of the living biological pest control agent are adhered to the interior surface of the cylindrical body section by a glue (e.g., a polyvinyl acetate and/or polyvinyl alcohol glue).

These and other aspects and advantages of the present invention will become more clear after careful consideration is given to the following detailed description of the preferred exemplary embodiments thereof.

BRIEF DESCRIPTION OF ACCOMPANYING DRAWINGS

Figure 2:
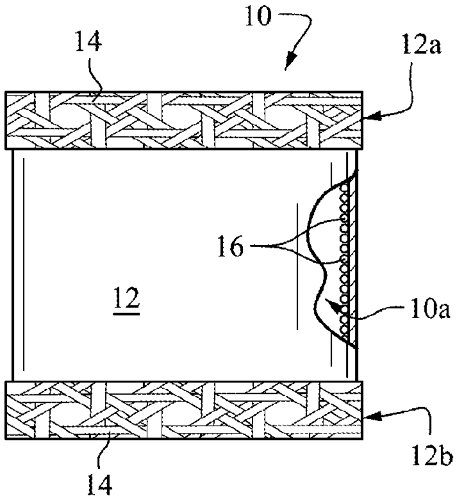
Figure 3:
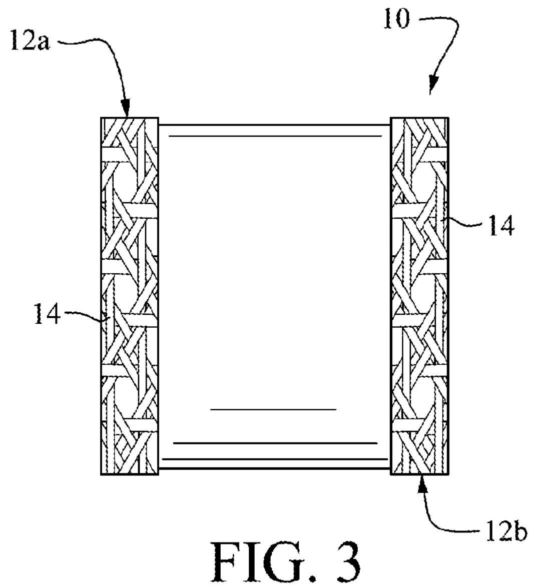
Figure 4:
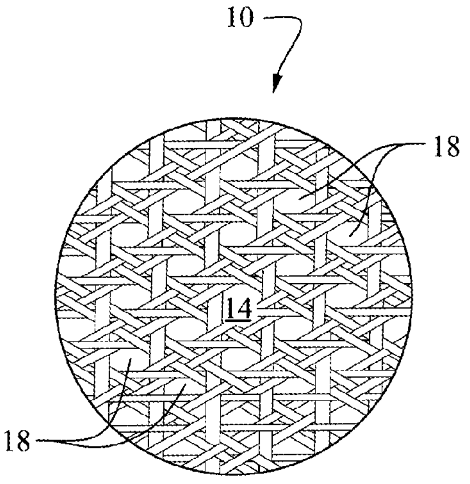
Figure 5:
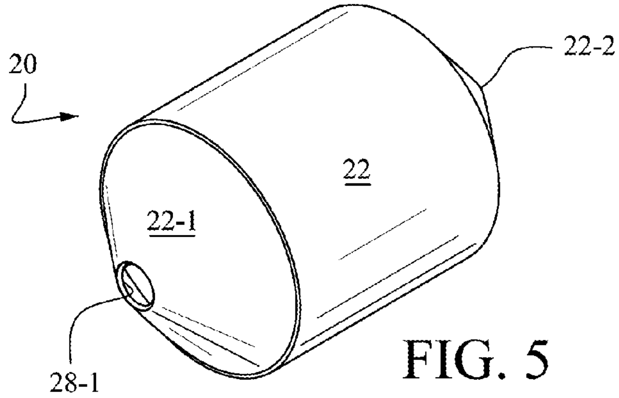
Figure 6:
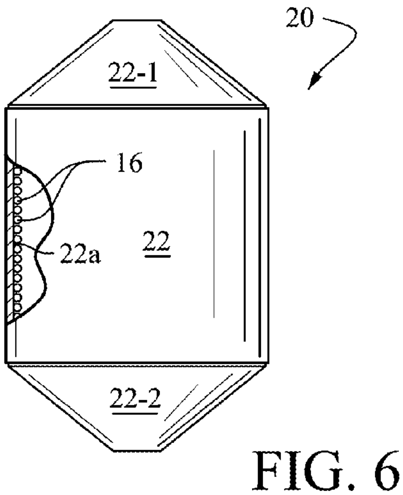
Figure 7:
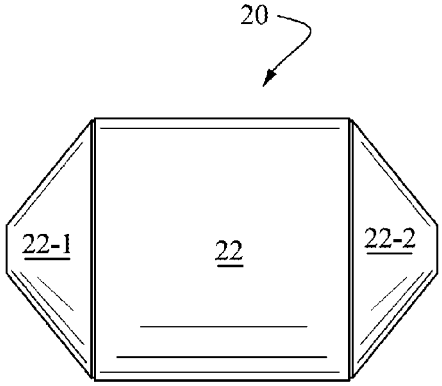
Figure 8:
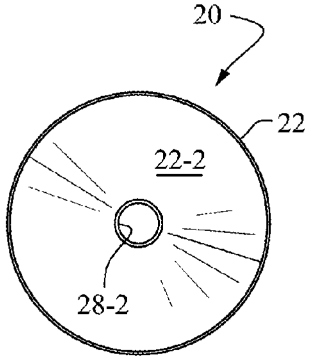
Figure 9:
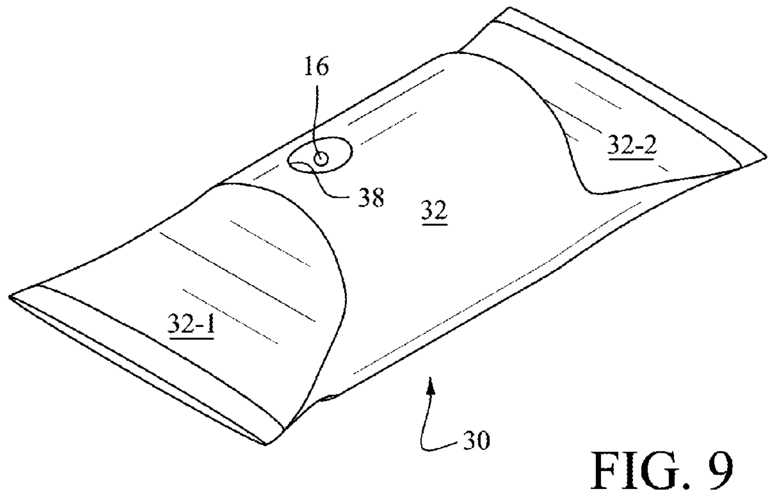
Figure 10:
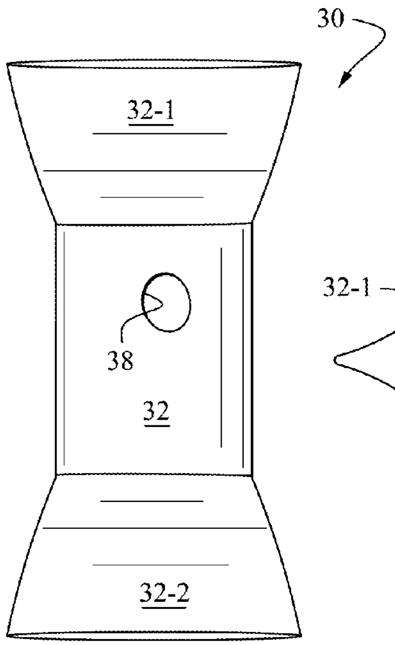
Figure 11:
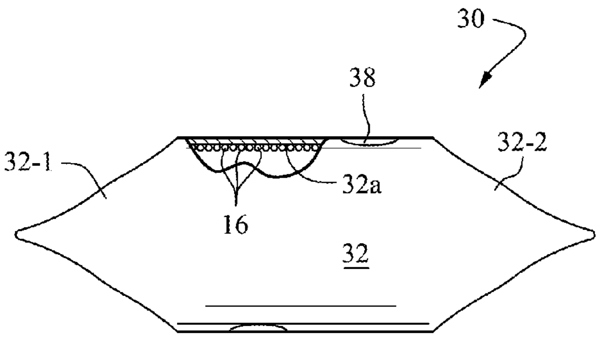
Figure 12:
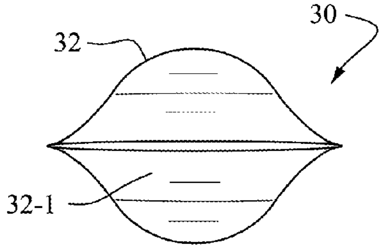
Figure 13:
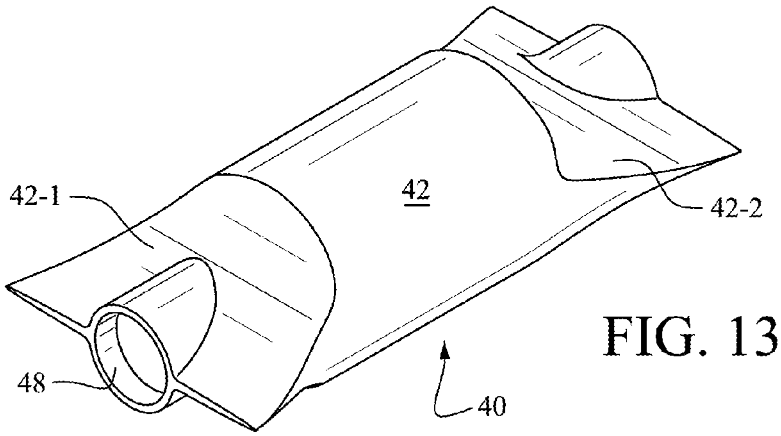
Figure 14:
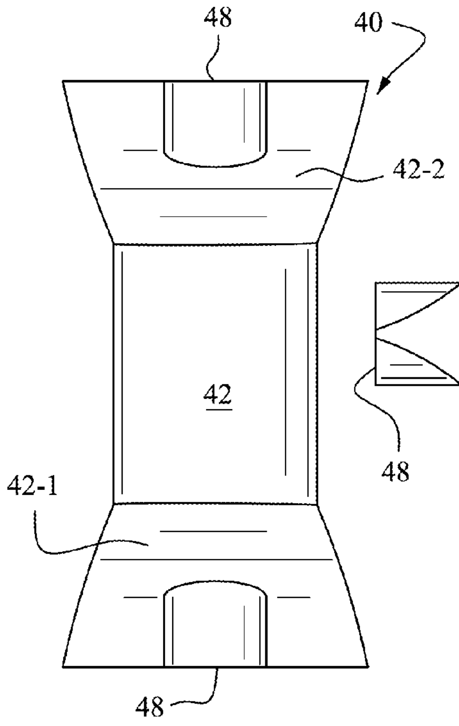
Figure 15:
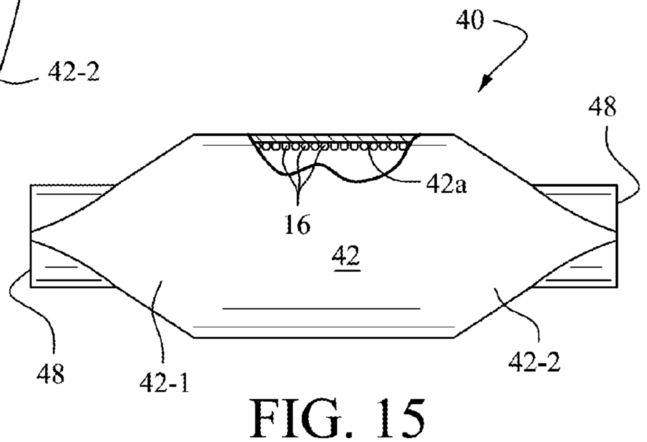
Figure 16:
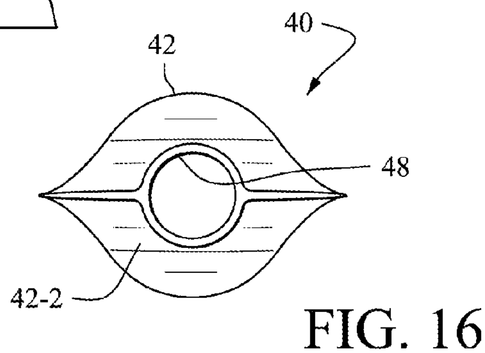

The disclosed embodiments of the present invention will be better and more completely understood by referring to the following detailed description of exemplary non-limiting illustrative embodiments in conjunction with the drawings of which:

FIGS. 1-4 depict various views of one embodiment of an enclosure for mass delivery of living biological agents according to the invention, wherein FIG. 1 is a vertical side perspective view thereof, FIG. 2 is a vertical side elevational view thereof, partly in section, FIG. 3 is a horizontal side elevational view thereof, and FIG. 4 is a top plan view thereof, the bottom plan view being a mirror image thereof;

FIGS. 5-8 depict various views of another embodiment of an enclosure for mass delivery of living biological agents according to the invention, wherein FIG. 5 is a perspective view thereof, FIG. 6 is a vertical side elevational view thereof, partly in section, FIG. 7 is a horizontal side elevational view thereof, and FIG. 8 is a top plan view thereof, the bottom plan view being a mirror image thereof;

FIGS. 9-12 depict various views of another embodiment of an enclosure for mass delivery of living biological agents according to the invention, wherein FIG. 9 is a perspective view thereof, FIG. 10 is a top plan view thereof, the bottom plan view being a mirror image thereof, FIG. 11 is a left side elevational view thereof, partly in section, and FIG. 12 is a left end elevational view thereof, the right end elevational view being a mirror image thereof; and FIGS. 13-16 depict various views of another embodiment of an enclosure for mass delivery of living biological agents according to the invention, wherein FIG. 13 is a perspective view thereof, FIG. 14 is a top plan view thereof, the bottom plan view being a mirror image thereof, FIG. 15 is a left side elevational view thereof, partly in section, the right side elevational view being a mirror image thereof, and FIG. 16 is a left end elevational view thereof, the right end elevational view being a mirror image thereof.

DETAILED DESCRIPTION

Accompanying FIGS. 1-4 shows one embodiment of an enclosure 10 for the mass delivery of a living biological pest control agent. In this regard, the enclosure 10 includes a generally cylindrical wall 12 formed of a biodegradable material (e.g., a biodegradable thermoplastic polymeric material, such as a cellulosic or starch-based polymeric material) having opposed ends 12*a*, 12*b* each of which is covered by a woven fabric 14.

The interior surface of the wall 12 is provided with a dense plurality of parasitized eggs (generally represented by reference numeral 16 in FIG. 2) of the living biological pest control agent (e.g., *Trichogramma*). The parasitized eggs 16 are most preferably adhered to the interior surface of the wall 12 by any conventional egg-compatible glue (e.g., polyvinyl acetate, polyvinyl alcohol and the like). Glues that are compatible with *Trichogramma* eggs are more fully disclosed by U.S. Pat. No. 3,442,845 (the entire content of which is expressly incorporated hereinto by reference).

As can be discerned from FIG. 1, the woven fabric 14 defines a plurality of openings (a few of which are identified by reference numeral 18 in FIGS. 1 and 4) that allow the endoparasitic insect to egress the interior 10*a* of the enclosure 10 and populate the exterior environment. The life cycle of endoparasitic insect will therefore perpetuate the continued parasitization of insect pest eggs thereby assisting in the control of such pests in a treated area.

Accompanying FIGS. 5-8 shows another embodiment of an enclosure 20 for the mass delivery of a living biological pest control agent. As seen, the enclosure 20 includes a generally cylindrical wall section 22 formed of a biodegradable material having opposed generally conically shaped necked ends 22-1, 22-2. A dense plurality of parasitized eggs 16 of the living biological pest control agent is adhered (glued) to the interior surface 22*a* of the cylindrical wall section 22. Each of the necked ends 22-1, 22-2 defines a respective egress openings 28-1, 28-2 (see FIGS. 5 and 8) that allow the endoparasitic insect to egress the interior of the enclosure 20 and populate the exterior environment.

Accompanying FIGS. 9-12 and 13-16 depict alternative embodiments of enclosures 30 and 40, respectively. In this regard, the enclosures 30 and 40 depicted in FIGS. 9-12 and 13-16 have a sachet geometry in that each of the ends 32-1, 32-2 and 42-1, 42-2 of the cylindrical wall section 32 and 42, respectively, is crimped closed. In each case, a dense plurality of parasitized eggs 16 of the living biological pest control agent is adhered (glued) to the interior surface 32*a*, 42*a* of the cylindrical wall sections 32 and 42, respectively. According to the embodiment of FIGS. 9-12, however, an egress opening 38 is formed through the wall section 32, whereas according to the embodiment of FIGS. 13-16, each of the crimped ends 42-1, 42-2 includes a respective egress opening 48.

The enclosures as described herein may be made by a process whereby an elongate generally cylindrical tubular member may be formed of the biodegradable polymer (e.g., by tubular extrusion). Although the geneally cylindrical tubular member may be formed in virtually any size that may be desired, it is currently envisioned that the cylindrical tubular member will have diameters and/or lengths of from about 0.5 mm up to about 100 millimeters. Typically, however, the diameter and/or lengths of the tubular member will be between about 1 to about 10 mm, e.g., about 5 mm. Larger or smaller cylindrical tubular members may be provided if desired, however. Similarly, the egress openings to allow the post-hatched parasitoid insect to leave the enclosure can vary within a relatively large size range, for example from about 0.1 mm up to about 20 mm, typically between about 0.5 mm to about 5 mm (e.g., about 1 mm).

The parasitized eggs of a living biological pest control agent may thereafter be adhered (glued) to an interior surface of the tubular member by any convenient means, e.g., by spraying, pad-coating or the like. Cutting the tubular member with the adhered parasitized eggs into discrete lengths either before or after the attachment of the parasitized egges will thereby provide a plurality of enclosure preforms having opposed ends that may be closed. At least one egress opening may then be provided (e.g., by drilling through the cylindrical wall or crimped end). The egress opening, e.g., according to the embodiment of FIGS. 13-16) may be formed concurrently by suitable tooling which cuts and crimps the ends of the cylindrical wall while simultaneously providing an egress opening at one or both of such crimped ends.

The completed enclosures with the parasitized eggs adhered to the interior surface thereof may then be delived in mass by various conventional techniques, e.g., by air dropping the enclosures via aircraft over the geographical area in the desired density to promote pest control.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope thereof.

What is claimed is:

1. An enclosure for mass delivery of a living biological pest control agent having a sachet geometry comprising:

a body section having a generally cylindrical wall portion defining an interior space by a generally cylindrical interior surface and opposed crimped end portions closing the interior space defined by the generally cylindrical wall portion;

parasitized eggs of a living biological pest control agent adhered to the interior surface of the generally cylindrical wall portion; and an opposed pair of generally cylindrical egress openings formed through the crimped end portions to establish communication between the interior space of the generally cylindrical wall portion and an exterior environment to thereby allow the living biological pest control agent to exit the body section to the exterior environment when hatched from the parasitized eggs.

2. The enclosure of claim 1, wherein the cylindrical wall portion is formed of a biodegradable polymer.

3. The enclosure of claim 1, wherein the parasitized eggs of the living biological pest control agent are adhered to the interior surface of the cylindrical body section by a glue.

* * * * *